United States Patent [19]

Hauser et al.

[11] Patent Number: 5,712,390

[45] Date of Patent: Jan. 27, 1998

[54] PROCESS FOR PREPARING 2-SUBSTITUTED BENZO [B] THIOPHENE COMPOUNDS AND INTERMEDIATES THEREOF

[75] Inventors: Kenneth L. Hauser, Greencastle; Alan D. Palkowitz, Carmel; Daniel J. Sall, Greenwood; Kenneth J. Thrasher, Indianapolis, all of Ind.

[73] Assignee: Eli Lilly and Company, Indianapolis, Ind.

[21] Appl. No.: 549,596

[22] Filed: Oct. 27, 1995

Related U.S. Application Data

[62] Division of Ser. No. 415,014, Mar. 31, 1995, Pat. No. 9,614,639.

[51] Int. Cl.[6] .............. C07D 409/12; C07D 413/12; C07D 333/52; C07D 333/56

[52] U.S. Cl. .............. 540/596; 544/146; 546/202; 548/571; 549/4; 549/49; 549/51; 549/57

[58] Field of Search .............. 549/4, 51, 49, 549/57; 540/596; 544/146; 546/202; 548/571

[56] References Cited

U.S. PATENT DOCUMENTS

| | | | |
|---|---|---|---|
| 4,133,814 | 1/1979 | Jones et al. | 260/326.5 |
| 4,358,593 | 11/1982 | Jones et al. | 546/202 |
| 4,380,635 | 4/1983 | Peters | 546/202 |
| 4,418,068 | 11/1983 | Jones | 546/202 |

OTHER PUBLICATIONS

Larock R.C., "Comprehensive Organic Transformations–Organoboron Reagents", p. 57, (1989).
Thompson et al., "A general synthesis of 5-Arylnicotinates", J.Org. Chem. 1984, 49, 5237–5243.
Oh–e et al., "Palladium–Catalyzed Cross–Coupling Reaction of Organoboron Compounds with Organic Triflates", J.Organ. Chem. 1993, 58, 2201–2208.
Graham, S.L., et al., *J. Med. Chem.*, 32(12) :2548–2554 (1989).
Lumma, W.C., et al., *J. Org. Chem.*,35(10) :3442–3444 (1970).
Suzuki, A, *Pure and Appl. Chem.*, 66(2) :213–222 (1994), (I).
Hoshino, Y., et al., *Bull. Chem. Soc. Jpn.*, 61: 3008–3010 (1988).
Suzuki, A., *Pure and Appl. Chem.*, 57(12) : 1749–1758.
Dickinson, R.P., et al., *J. Chem. Soc.*, (C) : 1926–1928 (1970).
Yates, J., et al., *Chem. Abs.*, 54 : 8851 (1960).

*Primary Examiner*—Deborah Lambkin
*Attorney, Agent, or Firm*—Jerry F. Janssen; David E. Boone

[57] ABSTRACT

The present invention provides processes for preparing compounds of formula I

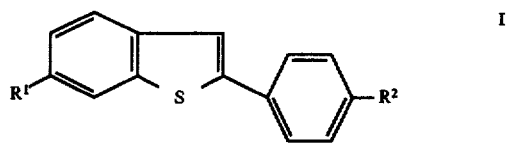

and for preparing compounds of formula VII

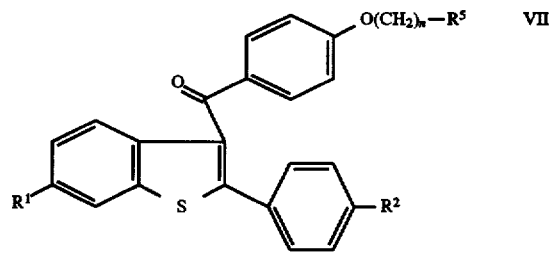

Also provided are processes for preparing compounds of formula VII in addition to intermediates of formula IX

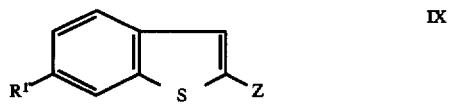

wherein $R^1$ is —OH, or —$OR^3$, in which $R^3$ is a hydroxy protecting group; and Z is bromo, iodo, triflate, or —$B(OH)_2$.

10 Claims, No Drawings

PROCESS FOR PREPARING 2-SUBSTITUTED BENZO [B] THIOPHENE COMPOUNDS AND INTERMEDIATES THEREOF

This application is a division of prior application Ser. No. 08/415,014, filed on Mar. 31, 1995 U.S. Pat. No. 5,614,639.

This invention relates to the fields of pharmaceutical and organic chemistry and provides processes for preparing 2-substituted benzo[b]thiophene compounds, some of which are useful as intermediates for preparing pharmaceutically active compounds, and others are useful, inter alia, for the treatment of osteoporosis in postmenopausal women.

Compounds of formula VII

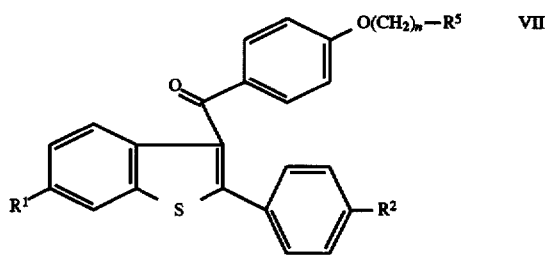

wherein $R^1$ is —H, —OH, or —$OR^3$, in which $R^3$ is a hydroxy protecting group;

$R^2$ is —H, —OH, or —$OR^4$, in which $R^4$ is a hydroxy protecting group;

$R^5$ is 1-piperidinyl, 1-pyrrolidinyl, methyl-1-pyrrolidinyl, dimethyl-1-pyrrolidinyl, 4-morpholino, dimethylamino, diethylamino, diisopropylamino, or 1-hexamethyleneimino;

n is 2 or 3, or a pharmaceutically acceptable salt thereof, are known as antifertility agents (see, e.g., U.S. Pat. No. 4,133,814). Certain formula VII compounds, particularly those in which $R^1$, $R^2$, and n are as defined above, and $R^5$ is 1-piperidinyl, 1-pyrrolidinyl, or 1-hexamethyleneimino, or a pharmaceutically acceptable salt thereof, are known to be useful for inhibiting bone loss in humans (see, e.g., U.S. Pat. No. 5,393,763). The compound known in the art as raloxifene, a formula VII compound in which $R^1$ and $R^2$ each are —OH, n is 2, and $R^5$ is 1-piperidinyl, or a pharmaceutically acceptable salt thereof, especially the hydrochloride salt, is a preferred product of the processes described herein.

Jones and Suarez, in U.S. Pat. No. 4,133,814, supra, first taught processes for preparing compounds of formula VII. In general, Jones, et al., prepared benzothiophenes of formula I

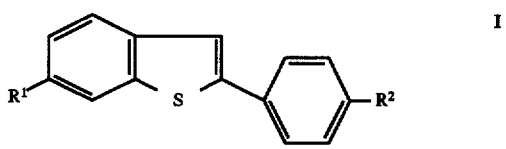

wherein $R^1$ is —H, —OH, or $OR^3$, in which $R^3$ is a hydroxy protecting group; and $R^2$ is —H, —OH, or $OR^4$, in which $R^4$ is a hydroxy protecting group, by first preparing a 2,3-dioxo-2,3-dihydrobenzothiophene of formula X

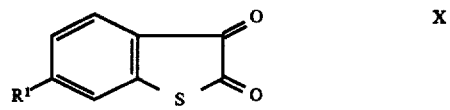

wherein $R^1$ is as defined above, and reacting a formula X compound with α-chlorophenylacetic acid, or an appropriately substituted derivative thereof, to form a diacid which is cyclized with a mixture of sodium acetate and acetic anhydride to give a compound of formula XI

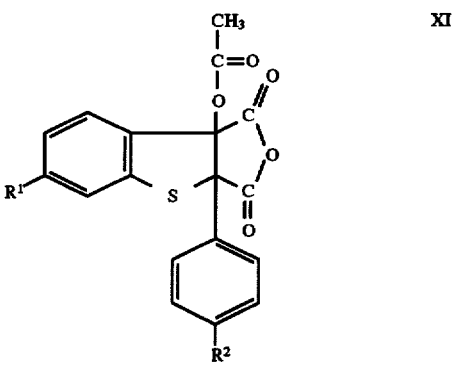

wherein $R^1$ and $R^2$ are as defined above. The formula XI compound is then hydrolyzed in the presence of sodium hydroxide to provide a compound of formula XII

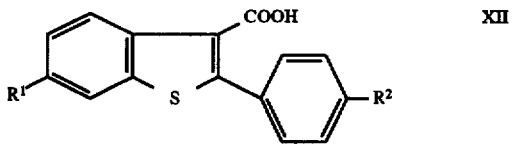

in which $R^1$ and $R^2$ are as defined above, which can finally be decarboxylated or used as such.

Because the Jones process for preparing formula I compounds of the present invention is costly and time consuming, a less expensive and more direct process for preparing compounds of formula I and, ultimately, compounds of formula VII, would be highly desirable and represent a significant advancement in the art. Accordingly, the present invention provides novel processes for preparing compounds of formulae I and VII, as well as novel intermediates therefore.

The present invention provides a process for preparing a compound of formula I

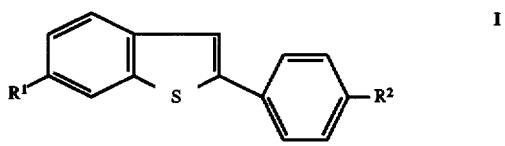

comprising a) forming a 2-position boronic acid derivative of a compound of formula II

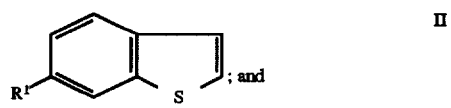

b) coupling the reaction product from step a), a compound of formula III with a compound of formula IV

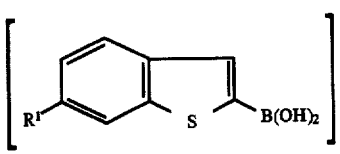

wherein

R¹ is —H, —OH, or OR³, in which R³ is a hydroxy protecting group;

R² is —H, —OH, or OR⁴, in which R⁴ is a hydroxy protecting group; and

X is bromo, iodo, or triflate.

The present invention further provides a process for preparing a compound of formula I

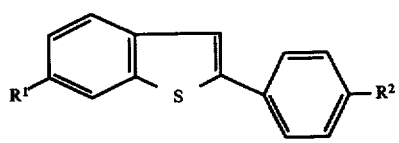

comprising a) selectively brominating or iodinating or forming a triflate leaving group at the 2-position of a compound of formula II

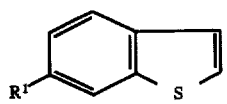

to provide a compound of formula V

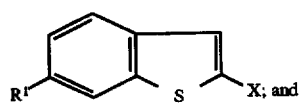

b) coupling said formula V compound with a compound of formula VI

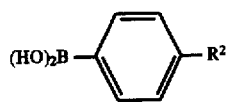

wherein

R¹ is —H, —OH, or OR³, in which R³ is a hydroxy protecting group;

R² is —H, —OH, or OR⁴, in which R⁴ is a hydroxy protecting group; and

X is bromo, iodo, or triflate.

In addition, the present invention provides methods of preparing a compound of formula I comprising steps a) and b) of either of the above-described processes of the present invention and further comprising c) acylating a compound of formula I with a compound of formula VIII

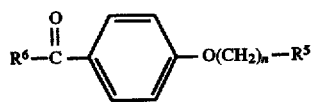

wherein

R¹ is —H, —OH, or OR³, in which R³ is a hydroxy protecting group;

R² is —H, —OH, or OR⁴, in which R⁴ is a hydroxy protecting group;

R⁵ is 1-piperidinyl, 1-pyrrolidinyl, methyl-1-pyrrolidinyl, dimethyl-1-pyrrolidinyl, 4-morpholino, dimethylamino, diethylamino, diisopropylamino, or 1-hexamethyleneimino;

R⁶ is bromo, chloro, iodo, or an activating ester group; and n is 2 or 3;

d) optionally removing the R³ and/or R⁴ hydroxy protecting groups; and e) optionally forming a pharmaceutically acceptable salt of said formula VII compound.

The present invention also provides compounds of formula IX

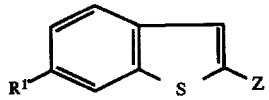

wherein

R¹' is —OH or —OR³, in which R³ is a hydroxy protecting group; and

Z is bromo, iodo, triflate, or —B(OH)₂, which are useful intermediates for the preparation of compounds of formulae I and VII of the present invention.

One aspect of the present invention provides convenient processes for preparing benzothiophene compounds of formula I.

The starting material for the instant process of the present invention, a compound of formula II

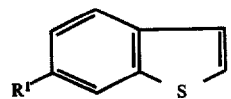

wherein R¹ is as defined above, is commercially available or is prepared via known procedures using known or commercially available materials [see, e.g., Graham, S. L., et al., *J. Med. Chem.*, 32(12):2548–2554 (1989)].

In the present, convenient process, an arylboronic acid derivative of a formula II compound is prepared, providing a compound of formula III, which is then coupled with an arene of formula IV, providing a compound of formula I. Alternatively, a formula II compound is selectively halogenated or a triflate leaving group is placed at the 2-position, providing a compound of formula V, which is then coupled with an arylboronic acid compound of formula VI providing a formula I compound. These reactions are shown in Route A and Route B, respectively, of Scheme I below.

Scheme I

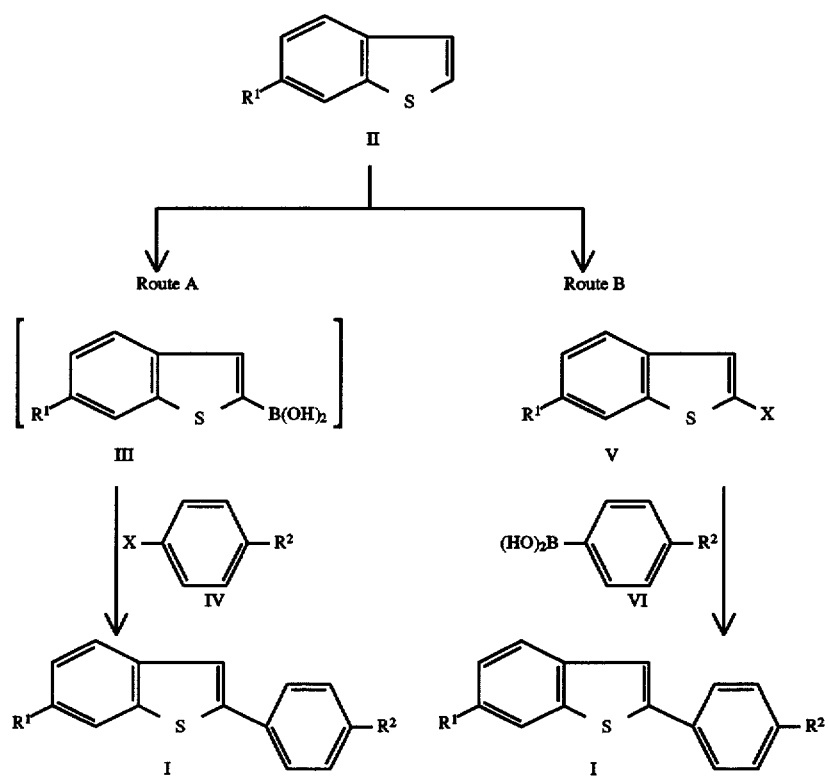

wherein $R^1$, $R^2$, and X are as defined above.

When $R^1$ and/or $R^2$ are $OR^3$ and $OR^4$, respectively, $R^3$ and $R^4$ represent hydroxy protecting groups which are moieties which generally are not found in the final, therapeutically active compounds of formula VII, but are intentionally introduced during a portion of the synthetic process to protect a group which otherwise might react in the course of chemical manipulations, and is then removed at a later stage of the synthesis. Because compounds bearing such protecting groups are important primarily as chemical intermediates (although some derivatives also exhibit biological activity), their precise structure is not critical. Numerous reactions for the formation, removal, and possibly, reformation of such protecting groups are described in a number of standard works including, for example, *Protective Groups in Organic Chemistry*, Plenum Press (London and New York, 1973); Green, T. W., *Protective Groups in Organic Synthesis*, Wiley New York, 1981; and *The Peptides*, Vol. I, Schrooder and Lubke, Academic Press (London and New York, 1965).

Representative hydroxy protecting groups include, for example, —$C_1$–$C_4$ alkyl, —CO—($C_1$–$C_6$ alkyl), —$SO_2$ ($C_4$–$C_6$ alkyl), and —CO—Ar in which Ar is optionally substituted phenyl. The term "substituted phenyl" refers to a phenyl group having one or more substituents selected from the group consisting of $C_1$–$C_4$ alkyl, $C_1$–$C_4$ alkoxy, hydroxy, nitro, halo, and tri(chloro or fluoro)methyl. Of these, methyl is highly preferred.

General chemical terms used above and throughout the present specification bear their usual meanings. For example, "$C_1$–$C_4$ alkyl" refers to straight or branched aliphatic chains of 1 to 4 carbon atoms including moieties such as methyl, ethyl, propyl, isopropyl, butyl, n-butyl, and the like. The term "halo" refers to bromo, chloro, fluoro, and iodo.

In the first step of Route A of Scheme I, a 2-position arylboronic acid of formula III is formed using standard procedures. Generally, a compound of formula II is treated with a slight excess of an n-alkyllithium in hexanes, in an appropriate solvent and, frequently, under an inert atmosphere such as nitrogen, followed by the slow or dropwise addition of an appropriate trialkylborane.

Appropriate solvents include an inert solvent or mixture of solvents such as, for example, diethyl ether, dioxane and tetrahydrofuran (THF). Of these, THF, particularly anhydrous THF, is preferred.

The preferred trialkylborate used in the present reaction is triisopropyl borate.

The product of this reaction, a compound of formula III, is then reacted with an aryl compound of formula IV, via standard Suzuki coupling procedures to provide compounds of formula I. Compounds of formula IV, in which $R^2$ is —H or $OR^3$, and $R^3$ is a hydroxy protecting group, are derived from commercially available compounds via procedures well known to one of ordinary skill in the art [see, e g., *Advanced Organic Chemistry: Reactions, Mechanisms, and Structure*, 4th Edition (J. March, ed., John Wiley and Sons, Inc., 1992); and Suzuki, A., *Pure and Appl. Chem.*, 6(2) :213–222 (1994)].

In the present coupling reaction, a slight excess of a formula IV compound is reacted with each equivalent of a formula III compound in the presence of a palladium catalyst and an appropriate base in an inert solvent such as toluene.

Although various palladium catalysts drive this coupling reaction, the catalyst selected usually is reaction specific. Thus, the use of tetrakis triphenylphosphine palladium in the present reaction is highly preferred.

Likewise, various bases may be used in the present coupling reaction. However, it is preferred to use an alkali metal carbonate, particularly 2N sodium carbonate.

The temperature employed in this step should be sufficient to effect completion of the coupling reaction. Typically, heating the reaction mixture to reflux for a period from about 2 to about 4 hours is adequate and preferred.

In Route B of Scheme I, the first step involves the 2-position bromination, iodination, or forming a triflate leaving group of a formula II compound using standard procedures. Generally, when brominating or iodinating, a formula II compound is reacted with a slight excess of n-butyllithium in hexane, in an appropriate solvent and, frequently under an inert atmosphere such as nitrogen, followed by the dropwise addition of a slight excess of the desired brominating or iodinating agent in an appropriate solvent. A preferred iodinating agent is iodine, and preferred brominating agents include bromine and N-bromosuccinimide.

Appropriate solvents include an inert solvent or mixture of solvents such as, for example, diethyl ether, dioxane, or THF. THF is preferred and anhydrous THF is especially preferred.

The present reaction is optionally run at a temperature range from about −75° C. to about −85° C.

The product of the above reaction, a halo arene of formula V, is then coupled with an arylboronic acid compound of formula VI, to provide compounds of formula I. The preferred reaction conditions for the coupling reaction are as described for the coupling reaction involving formula III and formula IV compounds in Route A of Scheme I above.

The processes shown in Scheme I and herein described may be carried out in separate steps in which the reaction product from each step is purified and characterized, or the process shown in Route A and the process shown in Route B is carried out in situ. Thus, the present processes, preferably, are each carried out in a single vessel.

Compounds of formula III and V, as shown in the present process, are novel when $R^1$ is —OH or —OR$^3$ and useful as intermediates for the preparation of pharmaceutically active compounds of formula VII, and are hereinafter collectively referred to as compounds of formula IX

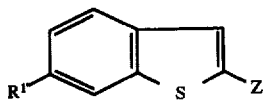

IX wherein $R^{1''}$ is —OH, or —OR$^3$, in which $R^3$ is a hydroxy protecting group; and Z is bromo, iodo, triflate, or —B(OH)$_2$.

In another aspect of the present invention, compounds of formula VII are prepared by a process comprising the process steps shown in Route A and Route B of Scheme I, and further comprising c) acylating a compound of formula I with a compound of formula VIII

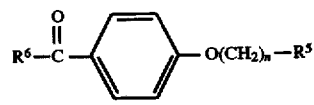

VIII wherein $R^1$ is —H, —OH, or OR$^3$, in which $R^3$ is a hydroxy protecting group;

$R^2$ is —H, —OH, or OR$^4$, in which $R^4$ is a hydroxy protecting group;

$R^5$ is 1-piperidinyl, 1-pyrrolidinyl, methyl-1-pyrrolidinyl, dimethyl-1-pyrrolidinyl, 4-morpholino, dimethylamino, diethylamino, diisopropylamino, or 1-hexamethyleneimino;

$R^6$ is bromo, chloro, iodo, or an activating ester group; and n is 2 or 3;

d) optionally removing the $R^3$ and/or $R^4$ hydroxy protecting groups; and e) optionally forming a pharmaceutically acceptable salt of said formula VII compound.

Process steps c), d), and e) are well known in the art individually or collectively and are described in U.S. Pat. Nos. 4,358,593, 4,418,068, 4,133,814, and 4,380,635, which are herein incorporated by reference.

Although the free-base form of formula VII compounds can be used for the aforementioned medical indications, it is preferred to prepare and use a pharmaceutically acceptable salt form. Thus, the formula VII compounds primarily form pharmaceutically acceptable acid addition salts with a wide variety of organic and inorganic acids, and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, ß-hydroxybutyrate, butyne-1, 4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The following examples are presented to further illustrate the preparation of compounds of the present invention. It is not intended that the invention be limited in scope by reason of any of the following examples.

NMR data for the following Examples were generated on a GE 300 MHz NMR instrument, and anhydrous d-6 DMSO was used as the solvent unless otherwise indicated.

EXAMPLE 1

6-methoxybenzo[b]thiophene-2-boronic acid

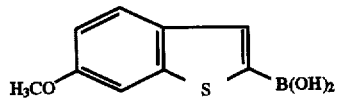

To a solution of 6-methoxybenzo[b]thiophene (18.13 g, 0.111 mol) in 150 mL of anhydrous tetrahydrofuran (THF) at −60° C. was added n-butyllithium (76.2 mL, 0.122 mol, 1.6M solution in hexanes), dropwise via syringe. After stirring for 30 minutes, triisopropyl borate (28.2 mL, 0.122 mol) was introduced via syringe. The resulting mixture was allowed to gradually warm to 0° C. and then distributed between 1N hydrochloric acid and ethyl acetate (300 mL each). The layers were separated, and the organic layer was dried over sodium sulfate. Concentration in vacuo produced a white solid that was triturated from ethyl ether hexanes. Filtration provided 16.4 g (71%) of 6-methoxybenzo[b]thiophene-2-boronic acid as a white solid. mp 200° C. (dec). $^1$H NMR (DMSO-d$_6$) d 7.83 (s, 1H), 7.78 (d, J=8.6 Hz, 1H), 7.51 (d, J=2.0 Hz, 1H), 6.97 (dd, J=8.6, 2.0 Hz, 1H), 3.82 (s, 3H). FD mass spec: 208.

Prepared in an analogous manner was benzo[b]thiophene-2-boronic acid (known compound).

EXAMPLE 2

[6-methoxy-2-(4-methoxyphenyl)]benzo[b]thiophene

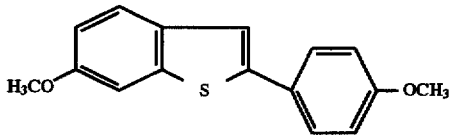

To a solution of 6-methoxybenzo[b]thiophene-2-boronic acid (1.00 g, 4.81 mmol) in toluene (20 mL) was added 4-iodoanisole (1.24 g, 5.29 mmol) followed by tetrakistriphenylphosphine palladium (0.17 g, 0.15 mmol). To this solution was added 5.0 mL of 2N sodium carbonate solution. The resulting mixture was heated to reflux for 2 hours. Upon cooling, a white precipitate ([6-methoxy-2-(4-methoxyphenyl)]benzo[b]thiophene) formed. The solid was collected by filtration and washed with ethyl acetate. The filtrate was distributed between ethyl acetate and saturated sodium bicarbonate solution. The layers were separated, and the organic layer was dried over sodium sulfate. Concentration in vacuo produced a white solid (additional [6-methoxy-2-(4-methoxyphenyl)]benzo[b]thiophene) that was collected by filtration. Total yield of product was 1.25 g (96%). mp 190°–194° C. $^1$H NMR (DMSO-d$_6$) δ7.71–7.63 (m, 3H), 7.61 (s, 1H), 7.53 (d, J=2.0 Hz, 1H), 7.03 (d, J=9.0 Hz, 2H), 6.99 (dd, J=9.0, 2.0 Hz, 1H), 3.83 (s, 3H), 3.81 (s, 3H). Anal. Calcd. for C$_{16}$H$_{14}$O$_2$S: C, 71.08; H, 5.22. Found: C, 71.24; H, 5.26.

Alternatively, purification was routinely achieved by chromatography on silicon dioxide.

Example 3

6-methyoxy-2-iodobenzo [b] thiophene

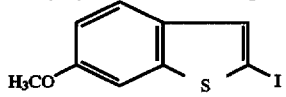

To a solution of 6-methoxybenzo[b]thiophene (5.00 g, 30.49 mmol) in 200 mL of anhydrous THF at −78° C., was added n-butyllithium (20.0 mL, 32.01 mmol, 1.6M solution in hexanes). After stirring for 15 minutes, a solution of I$_2$ (8.10 g, 32.01 mmol) in 25 mL of anhydrous THF was introduced dropwise via canula. The resulting mixture was allowed to gradually warm to ambient temperature. The reaction was quenched by distributing between ethyl acetate/brine (150 mL each). The layers were separated and the organic layer was dried over sodium sulfate. Concentration in vacuo produced a tan solid that was recrystallized from hexanes to provide 6.70 g (75%) of 6-methoxy-2-iodobenzo[b]thiophene. mp 75°–77° C. $^1$H NMR (CDCl$_3$) d 7.59 (d, J=8.6 Hz, 1H), 7.42 (s, 1H), 7.22 (d, J=2.0 Hz, 1H), 6.92 (dd, J=8.6, 2.0 Hz, 1H), 3.86 (s, 3H). FD mass spec: 290. Anal. Calcd. for C$_9$H$_7$OSI: C, 37.26; H, 2.43. Found: C, 37.55; H, 2.43.

6-methoxy-2-iodobenzo[b]thiophene was reacted with 4-methoxyphenylboronic acid according to the general procedure described above to provide [6-Methoxy-2-(4-methoxyphenyl)]benzo[b]thiophene in 80% yield.

We claim:

1. A process for preparing a compound of formula VII

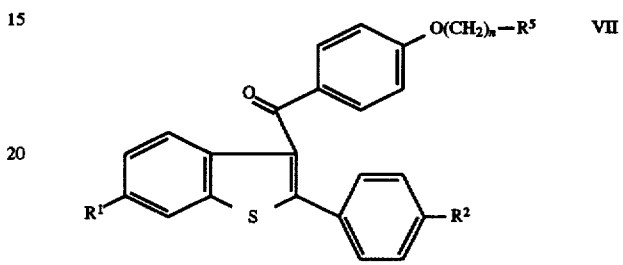

comprising a) forming a 2-position boronic acid derivative of a compound of formula II

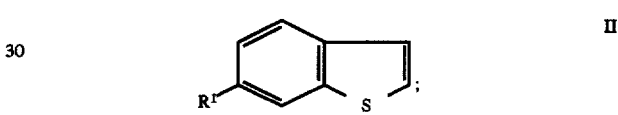

and b) coupling the reaction product from step a), a compound of formula III

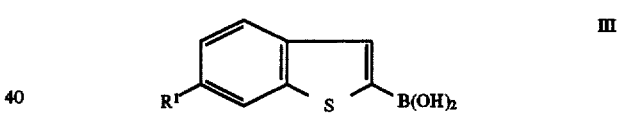

with a compound of formula IV

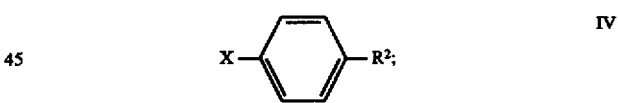

c) acylating the reaction product from step b) a compound of formula I

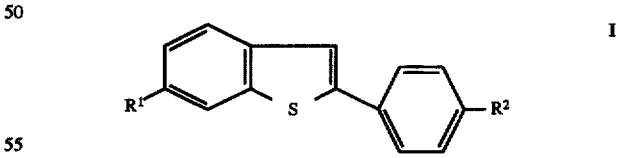

with a compound of formula VIII

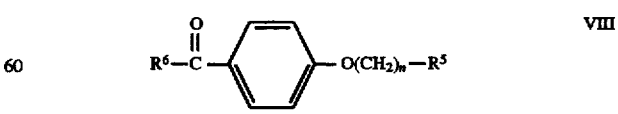

wherein

R$^1$ is —H, —OH, or —OR$^3$, in which R$^3$ is a hydroxy protecting group;

R$^2$ is —H, —OH, or OR$^4$, in which R$^4$ is a hydroxy protecting group;

$R^5$ is 1-piperidinyl, 1-pyrrolidinyl, methyl-1-pyrrolidinyl, dimethyl-1-pyrrolidinyl, 4-morpholino, dimethylamino, diethylamino, diisopropylamino, or 1-hexamethyleneimino;

$R^6$ is bromo, chloro, iodo, or an activating ester group;

n is 2 or 3; and

X is bromo, iodo, or triflate;

d) optionally removing the $R^3$ and/or $R^4$ hydroxy protecting groups; and e) optionally forming a pharmaceutically acceptable salt of said formula VII compound.

2. The process of claim 1 for preparing the intermediate compound of formula I

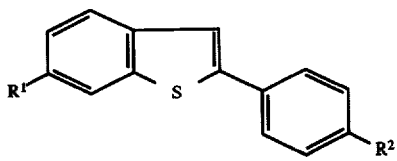

I wherein steps a) and b) of claim 1 are replaced by steps a) selectively brominating, iodinating or triflating a compound of formula II

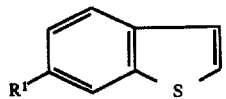

II to provide a compound of formula V

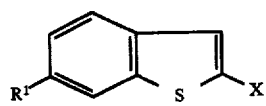

V and b) coupling the product of step a) with a compound of formula VI

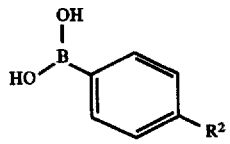

VI wherein $R^1$, $R^2$ and X are defined therein.

3. A process according to claim 2 wherein $R^1$ and $R^2$ of said formula VII compound each are —OH.

4. A process according to claim 3 wherein n is 2 and $R^5$ is 1-piperidinyl.

5. A process according to claim 4 wherein said pharmaceutically acceptable salt is the hydrochloride salt.

6. A process according to claim 5 wherein $R^6$ is bromo or chloro.

7. A process according to claim 1 wherein $R^1$ and $R^2$ of said formula VII compound each are —OH.

8. A process according to claim 7 wherein n is 2 and $R^5$ is 1-piperidinyl.

9. A process according to claim 8 wherein said pharmaceutically acceptable salt is the hydrochloride salt.

10. A process according to claim 9 wherein $R^6$ is bromo or chloro.

* * * * *

UNITED STATES PATENT AND TRADEMARK OFFICE
CERTIFICATE OF CORRECTION

PATENT NO. : 5,712,390
DATED : January 27, 1998
INVENTOR(S) : Kenneth L. Hauser, et al.

It is certified that error appears in the above-identified patent and that said Letters Patent is hereby corrected as shown below:

In column 1, line 7, please insert the word -- pending -- before the phrase "prior application Ser. No."

In column 8, line 32, please replace the term "62" with the symbol -- ß --

Signed and Sealed this

Twenty-seventh Day of October, 1998

Attest:

BRUCE LEHMAN

*Attesting Officer*  *Commissioner of Patents and Trademarks*